(12) United States Patent
Keri et al.

(10) Patent No.: US 7,232,486 B2
(45) Date of Patent: Jun. 19, 2007

(54) CRYSTALLIZATION AND PURIFICATION OF MACROLIDES

(75) Inventors: Vilmos Keri, Debrecen (HU); Andrea Csorvasi, Debrecen (HU)

(73) Assignee: TEVA Gyógyszergyár Zártkörűen Működő Részvénytársaság, Debrecen (HU)

( * ) Notice: Subject to any disclaimer, the term of this patent is extended or adjusted under 35 U.S.C. 154(b) by 201 days.

(21) Appl. No.: 10/815,339

(22) Filed: Mar. 31, 2004

(65) Prior Publication Data

US 2004/0226501 A1 Nov. 18, 2004

Related U.S. Application Data

(60) Provisional application No. 60/512,887, filed on Oct. 20, 2003, provisional application No. 60/461,707, filed on Apr. 9, 2003, provisional application No. 60/459,591, filed on Mar. 31, 2003.

(51) Int. Cl.
*C30B 7/14* (2006.01)

(52) U.S. Cl. .............................. 117/68; 117/69; 117/70; 117/924; 117/926

(58) Field of Classification Search ................. 117/68, 117/69, 70, 924, 926
See application file for complete search history.

(56) References Cited

U.S. PATENT DOCUMENTS

| | | | |
|---|---|---|---|
| 3,993,749 A | 11/1976 | Sehgal et al. | |
| 4,160,861 A | 7/1979 | Cole et al. | |
| 4,543,334 A * | 9/1985 | Celmer et al. ........... | 435/253.5 |
| 4,894,366 A | 1/1990 | Okuhara et al. | |
| 5,091,389 A | 2/1992 | Ondeyka et al. | |
| 5,116,756 A | 5/1992 | Dumont et al. | |
| 5,200,505 A | 4/1993 | Takesako et al. | |
| 5,496,727 A | 3/1996 | Okuhara et al. | |
| 5,506,233 A | 4/1996 | Hauske et al. | |
| 5,508,398 A * | 4/1996 | Gletsos ........................ | 540/456 |
| 5,622,866 A | 4/1997 | Motamedi et al. | |
| 5,624,842 A | 4/1997 | Okuhara et al. | |
| 6,387,258 B1 | 5/2002 | Keri et al. | |
| 2002/0128470 A1 | 9/2002 | Fuenfschilling et al. | |
| 2003/0166924 A1* | 9/2003 | Keri et al. .................. | 540/458 |
| 2004/0050782 A1 | 3/2004 | Fuenfschilling et al. | |
| 2004/0266703 A1* | 12/2004 | Keri et al. ..................... | 514/29 |

FOREIGN PATENT DOCUMENTS

| | | |
|---|---|---|
| CH | 692 839 A5 | 11/2002 |
| DE | 2121517 | 11/1972 |
| EP | 0 184 162 | 6/1986 |
| EP | 0 652 219 A1 | 5/1995 |
| EP | 1 234 833 A2 | 8/2002 |
| WO | WO 92/18506 | 10/1992 |
| WO | WO 00/33878 | 6/2000 |

OTHER PUBLICATIONS

Patent Abstract of Japan Publication No. 02016662; Publication date Jan. 19, 1990; Akashi Kazuya "Substituting Terminal Controller".

Surjit S. Sengha, Fermentation, in Kirk Othmer Encyclopedia of Chemical Technology, vol. 10, p. 361-381 (Jacquiline I. Kroschwitz, editor, 4th ed. 1993).

The Merck Index, Maryadele J. O'Neil et al. eds., "Pirnecrolimus", p. 1331, 13th ed. 2001.

Martindale: The complete drug reference, Sean C. Sweetman ed., "Sirolimus", p. 568, Pharmaceutical Press 33rd ed. 2002.

C.E.M. Griffiths "Ascomycin: An Advance in the Management of Atopic Dermatitis" British J. of Dermatology, V. 144, p. 679-681, (2001).

Martindale: The compete drug reference, Sean C. Sweetman ed., "Everolimus", p. 539, Pharmaceutical Press 33rd ed. 2002.

Zhiguo Song et al. "Highly Chemoselective Trichloracetimidate-Mediated Alkylation of Ascomycin: A Convergent, Practical Synthesis of the Immunosuppressant L-733,725" J. Org. Chem. 1999, v. 64, p. 1859-1867.

Jun'ichi Kobayashi et al. "Amphidinolides T2, T3, and T4, New 19-Membered Macrolides from the *Dinoflagellate amphidinium* sp. and the Biosynthesis of Amphidinolide T1" J. Org. Chem. 2001, v. 66, p. 134-142.

K. Yoshii et al. "Liquid Chromatographic Determination of Emamectin, Milbemectin, Invermectin and Abamectin in Crops and Confirmation by Liquid Chromatography—Mass Spectrometry" Journal of Chromatography A, v. 896, 2000, p. 75-85.

* cited by examiner

*Primary Examiner*—Robert Kunemund
(74) *Attorney, Agent, or Firm*—Kenyon & Kenyon LLP

(57) ABSTRACT

Provided is a method for crystallization and purification of a macrolide such as tacrolimus, sirolimus, pimecrolimus, or everolimus that includes the step of providing a combination of a macrolide, and a polar solvent, dopolar aprotic solvent, or hydrocarbon solvent at pH of 7 or above.

36 Claims, No Drawings

CRYSTALLIZATION AND PURIFICATION OF MACROLIDES

RELATED APPLICATIONS

The present application claims the benefit of the filing date of the following U.S. Provisional Patent Applications: U.S. provisional application Ser. No. 60/512,887, filed Oct, 20, 2003, U.S. provisional application Ser. No. 60/461,707, filed Apr. 9, 2003, and U.S. provisional application Ser. No. 60/459,591, filed Mar. 31, 2003, the contents of all of which are incorporated herein.

FIELD OF THE INVENTION

The present invention relates to the crystallization and purification of macrolides, especially tacrolimus, sirolimus (rapamycin), pimecrolimus, and everolimus.

SUMMARY OF THE INVENTION

The present invention relates to a method for crystallization and purification of macrolides, especially tacrolimus, sirolimus, pimecrolimus, and everolimus, including the steps of: providing a combination of a macrolide starting material; a polar solvent, especially a polar solvent that is an alkyl ester of an alkanoic acid, an alcohol, an ether, an aliphatic ketone, an aliphatic nitrile, or a dipolar aprotic solvent; a hydrocarbon solvent, especially an acyclic or cyclic aliphatic hydrocarbon or an aromatic hydrocarbon (e.g. toluene); and water; at a pH of about 7 or above, especially about 8 or above; maintaining the combination at a temperature of between about −15° C. to about 50° C., preferably between about −5° C. to about 40° C. , most preferably between about −2° C. to about 35° C. for at least about 1 hour, preferably between about 48 to about 100 hours; and isolating crystalline macrolide.

In another aspect, the present invention relates to a method for crystallization and purification of a macrolide, especially tacrolimus, sirolimus, pimecrolimus, or everolimus including the steps of: providing a concentrate residue from whole-broth extraction of macrolide-containing biomatter in a polar solvent, especially a polar solvent that is an alkyl ester of an alkanoic acid, an alcohol, an ether, an aliphatic ketone, an aliphatic nitrile, or a dipolar aprotic solvent; combining the solution, in any order, with water and a hydrocarbon solvent, especially an acyclic or cyclic aliphatic hydrocarbon or an aromatic hydrocarbon (e.g. toluene), wherein the pH is about 7 or above, especially about 8 or above; maintaining the combination at a crystallization temperature for a crystallization time; and isolating crystalline macrolide.

In a further aspect, the present invention relates to a method of crystallizing and purifying a macrolide, especially tacrolimus, sirolimus, pimecrolimus, or everolimus including the steps of: combining, in any order, an oil that is a concentrate obtained by concentrating a solution obtained by extracting macrolide-containing biomatter with a hydrophobic extraction solvent, e.g. butyl acetate; with a polar solvent, especially a polar solvent that is an alkyl ester of an alkanoic acid, an alcohol, an ether, an aliphatic ketone, an aliphatic nitrile, or a dipolar aprotic solvent; a hydrocarbon solvent, especially an acyclic or cyclic aliphatic hydrocarbon or an aromatic hydrocarbon (e.g. toluene); and water; wherein the pH is about 7 or above, especially 8 or above; maintaining the combination at a first crystallization temperature for a first crystallization time; and isolating crystalline macrolide.

In any of the forgoing aspects, the combination can be, but need not be, maintained at a second crystallization temperature for a second crystallization time.

DETAILED DESCRIPTION OF THE INVENTION

As used herein in connection with a measured quantity, "about" refers to that variation in the measured quantity as would be expected by the skilled artisan performing or interpreting the measurement and exercising a level of care commensurate with the objective of the measurement and the precision of the measuring equipment being used.

As used herein, ambient temperature refers to a temperature of about 18° C. to about 25° C.

As used herein, "RN" refers to the registry number assigned to a chemical compound by the Chemical Abstracts Service, Columbus Ohio, USA).

The method of the present invention is applied to the crystallization and purification of macrolides from macrolide-containing starting material. The macrolides are multi-membered lactone rings having one or more deoxy sugars as substituents. Erythromycin, azithromycin, and clarithromycin are macrolides that have bacteriostatic and/or bactericidal activity. The macrolides tacrolimus (FK 506) and sirolimus (rapamycin) are preferred macrolides for use in the practice of the present invention. The macrolides pimecrolimus (the 33-epichloro derivative of ascomycin; RN=137071-32-0) and everolimus (40-O-(2-hydroxyethyl)-rapamycin; RN=159351-69-6) are also preferred macrolides for use in the practice of the present invention.

The macrolides are typically obtained by fermentation, although synthetic routes to some are known. The macrolide starting material for use in the practice of the present invention can be from any source. Concentrate residue from concentrating the extract of the entire fermentation broth ("whole broth method") from macrolide-containing biomatter can be used as the macrolide starting material for the present method. Use of hydrophobic extraction solvent in the extraction to obtain solution to be concentrated results in an efficient extraction yield, leaving behind most water-soluble impurities, with removal of mycelium in one step. Concentration under reduced pressure at T>25° C. and reduced pressure results in a high evaporation rate of solvent without precipitation or decomposition of macrolide and provides a macrolide starting material for use in the practice of the present invention. Concentrate residue for use as macrolide starting material in the practice of the present invention can be obtained as described in U.S. patent application Ser. No. 10/366,266, published as U.S. 2003/01666924 A1 and incorporated herein in its entirety by reference.

Oily residue from macrolide-producing procedsses can also be used as starting macrolide starting material.

Preferred macrolide-containing biomatter that can be a source of macrolide starting material for the practice of the present invention includes tacrolimus-containing biomatter, particularly fermentation broth obtainable by fermentation using a tacrolimus-producing microorganism, for example, *Streptomyces tsukubaensis*, new and mutated strains thereof, *Streptomyces hygroscopicus*, and *Streptomyces lividans*, as described in U.S. Pat. Nos. 4,894,366, 5,116,756, 5,624,842, 5,496,727, and 5,622,866, all of which are incorporated herein by reference. Sirolimus-containing (rapamycin-containing) biomatter is also a preferred macrolide-containing biomatter. Sirolimus (rapamycin) can be produced by fermentation of *Streptomyces hygroscopicus*, NRRL 5491, as described in U.S. Pat. No. 3,993,749, incorporated herein by reference. Pimecrolimus-containing biomatter and everolimus-containing biomatter are also examples of preferred macrolide-contaiing biomatter for use in the practice of the method of the present invention. Ascomycin-containing biomatter is also a preferred macrolide-containing biomatter for use in the practice of the present invention.

The method of the present invention employs, among other things, polar solvents, hydrocarbon solvents, and bases (alkali).

Polar solvents are organic compounds, normally liquid at ambient temperature, that dissolve a macrolide, especially tacrolimus, sirolimus, pimecrolimus, or everolimus. Polar solvents useful in the practice of the present invention include esters, alcohols, aliphatic nitriles, acyclic and cyclic aliphatic ethers, aliphatic ketones, and dipolar aprotic solvents.

Esters useful in the practice of the present invention have the general formula $R_1$—C(O)O—$R_2$, wherein $R_1$ is H or linear or branched C1–6 alkyl, and $R_2$ is linear or branched C1–6 alkyl. Examples of esters include methyl acetate, ethyl acetate, n-propyl acetate, iso-propyl acetate, n-butyl acetate, iso-butyl acetate, methyl formate, n-propyl formate, iso-propyl formate, n-butyl formate, and iso-butyl formate, to mention just a few. Alcohols (alkanols, glycols, and aromatic alcohols) useful in the practice of the present invention include methanol, ethanol, n-propanol, iso-propanol, ethylene glycol, propylene glycol, polyethylene glycol, polypropylene glycol, amyl alcohol and benzyl alcohol, to mention just a few.

Aliphatic ketones useful in the practice of the present invention have the general formula $R_1$—C(O)—$R_2$, wherein $R_1$ and $R_2$ are, independently, linear or branched alkyl groups, each having from 1 to 4 carbon atoms. Examples of aliphatic ketones include acetone, methyl ethyl ketone, and methyl iso-butyl ketone, to mention just three.

Examples of aliphatic nitriles useful in the practice of the present invention include acetonitrile, propionitrile, and butyronitrile, to mention just three.

Ethers useful in the practice of the present invention include both acyclic and cyclic aliphatic ethers. Acyclic aliphatic ethers have the general formula $R_1$—O—$R_2$, wherein $R_1$ and $R_2$ are as defined above. Examples of acyclic aliphatic ethers include diethyl ether, di-n-propyl ether, and ethyl n-propyl ether, to mention just a few. Tetrahydrofuran and the dioxanes are examples of cyclic aliphatic ethers useful in the practice of the present invention.

Dipolar aprotic solvents are well known to the skilled artisan. Dimethyl acetamide (DMAC), dimethyl formamide (DMF), N-methyl-2-pyrrolidone (NMT), acatamide, dioxane and dioxalane are examples of dipolar aprotic solvents useful in the practice of the present invention.

Hydrocarbon solvents are organic compounds, normally liquid at ambient temperature, that are poor solvents for macrolides. The hydrocarbon solvents can be aliphatic hydrocarbon solvents, or they can be aromatic hydrocarbon solvents.

The aliphatic hydrocarbon solvents can be acyclic or they can be cyclic. Acyclic hydrocarbon solvents can be linear or branched and have the general formula $C_nH_{2n+2}$, where n is from about 5 to about 10. n-Hexane, n-heptane, octane and iso-octane are examples of preferred acyclic aliphatic hydrocarbon solvents. Cyclohexane and methylcyclohexane are examples of cyclic aliphatic hydrocarbon solvents. Examples of aromatic hydrocarbon solvents include benzene, toluene, the xylenes, and the tetralins, to mention just a few.

Any base, organic or inorganic, can be used in the practice of the present invention. Examples of inorganic bases include ammonia, alkali and alkaline earth metal hydroxides, bicarbonates, and carbonates, to mention just a few. The amines are examples of organic bases that can be used in the practice of the present invention.

The present invention provides a method for crystallization and purification of a macrolide, preferably tacrolimus, sirolimus, pimecrolimus, or everolimus including the steps of: providing, in a crystallization vessel, a combination of a macrolide starting material, a polar solvent, a hydrocarbon solvent, and water, whereby a water rich phase is formed. A water-rich phase is a phase in with the majority of the solvent is water and can contain other solvents and solutes. The pH of the water-rich phase is or is adjusted to be about 7 or above, preferably about 8 or above. The pH can be adjusted by addition of base.

The combination is provided, preferably with agitation, and is maintained at a temperature of between about −15° C. to about 50° C., preferably between about −5° C. to about 40° C., most preferably between about −2° C. to about 35° C. for at least about 1 hour, preferably between about 48 to about 100 hours, whereby a macrolide-rich phase forms.

The manner in which the provided combination is assembled is irrelevant to the practice of the present invention. The components of the combination can be assembled in any order, or they can be assembled simultaneously.

The combination of macrolide, polar solvent, hydrocarbon solvent, and water is provided in a crystallization vessel (crystallization space) provided with an agitator. The design and peculiar characteristics of the crystallization vessel are unimportant and the skilled artisan will know to select the crystallization vessel and agitator based on, among other things, the volume of the combination and the process variables.

At the start of the first crystallization time, the combination provided will include two or more phases, at least one of which is water-rich. The pH of the water-rich phase is about 7 or above, preferably about 8 or above. The pH of the water-rich phase can be constant throughout the total crystallization time, or it can be varied in the course of the crystallization time, provided the pH is always at least about 7 or above.

The desired pH is established with the use of any available inorganic or organic base and the desired pH can be established in any manner or sequence. For example, the pH of the water used to assemble the combination can be adjusted, prior to assembly of the combination, with an inorganic or organic base. Thus, as used herein in connection with the combination provided, "water" will be understood to include dilute aqueous solutions (water solutions) of inorganic or organic bases, e.g., N/10 $NaOH_{aq}$, N/10 KOH, N/10 Ca(OH)$_2$, N/10 $NH_{3aq}$, N/10 $(C_2H_5)_3N_{aq}$, N/10 diethylamine or triethyl amine, N/10 pyridine etc. Base can be added before the water-rich phase is established by, for example, admitting a low-boiling amine, e.g. methylamine, before water is introduced. The skilled artisan will recognize a plethora of alternatives to establishing the desired pH of the water-rich phase.

The pH can be adjusted after the combination is assembled by adding inorganic base, neat, especially as a gas, or in solution in a suitable solvent, e.g. water. The pH can be adjusted in increments. For example, the pH of the water used to assemble the combination can be adjusted to, e.g., ca. 7 before the combination is assembled and, after assembly, the pH of the water-rich phase can be further adjusted, e.g. to pH 8, by the addition of base, neat or in solution.

During the course of the total crystallization time, at least one macrolide-rich phase develops, from which the macrolide crystallizes, substantially free of impurities. At the end of the total crystallization time, crystalline macrolide is isolated by any of the common methods, for example filtration (gravity or pressure-assisted) or centrifugation, to mention just two. The purity of the isolated crystalline macrolide rivals that of macrolide purified by multiple-pass chromatography.

In one embodiment, the combination provided is assembled by the steps of providing macrolide starting material that is a solution of macrolide, or a concentrate from macrolide extraction, preferably tacrolimus, sirolimus, pimecrolimus, or everolimus in a polar solvent and combining the solution, in any order, with hydrocarbon solvent and water.

The solution provided can be made by any means or method. The concentration of the solution provided is not critical and will generally be between about 0.05 g/mL (g macrolide per mL polar solvent) and about 0.3 g/mL. The macrolide can come from any source and can be a solid, semi-solid, or an oil (especially an oil that is a residue from concentration of extract from a whole-broth extraction of macrolide-containing biomatter).

The relative volumes of solution, water, and hydrocarbon solvent are not critical. Typically, the ratio of the volume of solution to the volume of hydrocarbon solvent will be between about 1:2 and about 1:10. The ratio of the volume of solution to the volume of water will typically be between about 1:8 to about 1:25.

The pH of the water-rich phase can be adjusted and the combination treated as described above.

In another embodiment, the combination provided is assembled by combining, in any order, macrolide starting material, preferably tacrolimus, sirolimus, pimecrolimus, or everolimus starting material, hydrocarbon solvent, polar solvent, and water, wherein the tacrolimus starting material is an oily phase that is a concentrate obtained by concentrating a solution obtained by extracting macrolide-containing biomatter with a hydrophobic extraction solvent, especially wherein the hydrophobic extraction solvent is selected from the group consisting of C2–C6 linear and branched esters of acetic acid or formic acid, C3–C6 linear or branched aliphatic ketones, halogenated methanes, and aromatic hydrocarbons that are liquid at 25° C. and that have a boiling point at atmospheric pressure less than about 150° C., wherein the extraction is at a temperature between about 2° C. to about 70° C., especially between about 30° C. and about 70° C., and at a pH of between about 5.5 and about 13, especially between about 7.5 and about 13, to obtain the solution of the macrolide in the hydrophobic extraction solvent.

The oil (macrolide starting material) can first be combined with polar solvent or hydrocarbon solvent or water. The order is irrelevant to the practice of the present invention. The base required to establish the desired pH can be introduced at any point, or at several points prior to or during the crystallization time. The base can be introduced neat, or as a solution, e.g. a solution in water.

The present invention, in certain of its embodiments, is illustrated by the following non-limiting examples.

EXAMPLE 1

Extraction:

Fermentation broth (22.2 m$^3$) containing tacrolimus (3.42 kg) was extracted with 6.4 m$^3$ iso-butyl acetate at pH between 9.0–9.5. The iso-butyl acetate solution was washed with water at pH between 6.0–8.0. The washed iso-butyl acetate phase was concentrated to oily-like residue under reduced pressure at temperature between 40–45° C.

The oily-like residue was dissolved with iso-butyl acetate to a volume of 31 L. This concentrate was diluted with 167.5 L methanol and 18.6 L water. The water-methanol solution was washed with 139.6 L n-Hexane. The water-methanol phase was concentrated under reduced pressure to volume of 44 L, and the concentrate was diluted with 44 L water.

The obtained mixture was extracted with 88 L ethyl acetate. The ethyl acetate extract was concentrated to volume of 22.4 L.

Crystallization:

This concentrate of ethyl acetate extract was combined with 158.4 L 0.1 M aqueous triethyl amine solution and with 67.3 L n-Hexane. The mixture was stirred at 20°–25° C. for 3 hours. The mixture was let to stand at 0°–25° C. for 48 hours (1 minute stirring every hour).

The crystals formed were isolated by filtration and were suspended first in 83 L 0,1 M aqueous triethyl amine solution and, second, in 83 L n-Hexane. The crystals were isolated by filtration.

The crystals were dried at 40° C. under reduced pressure. The dried crude tacrolimus had an assay 83%. Crude product contains 1.9 kg tacrolimus.

The yield of the crystallization step was 91%.

EXAMPLE 2

In the following example, a macrolide (tacrolimus), as an oily concentrate from whole-broth extraction of macrolide-containing biomatter, was combined with polar solvent, hydrocarbon solvent, and water containing a base. The combination was held at a crystallization temperature for a total crystallization time. At the end of the total crystallization time, the crystalline macrolide was isolated. The proportions of components, the process variables, and the results are collected in Table I.

TABLE I

| Number of experiment | Concentrate | Tacrolimus content | Polar solvent | Hydrocarbon solvent | Water | Total $t_C$ (hr) | $T_C$ (° C.) | Yield | Assay |
|---|---|---|---|---|---|---|---|---|---|
| 1 | 15.23 g | 1.42 g | Ethyl acetate 30.3 ml | n-Hexane 60.7 ml | 0.1 N NaOH 273 ml | 24 | +50–+20 | 41.82% | 84.65% |
| 2 | 14.36 g | 1.42 g | Ethyl acetate 12.3 ml | n-Hexane 73.7 ml | 0.1 N NaOH 172 ml | 20 | +25–0 | 78.48% | 81.68% |
| 3 | 13.67 g | 1.42 g | Ethyl acetate 7.5 ml | n-Hexane 74.5 ml | 0.1 N NaOH 164 ml | 20 | +25–0 | 79.06% | 81.74% |

TABLE I-continued

| Number of experiment | Concentrate | Tacrolimus content | Polar solvent | Hydrocarbon solvent | Water | Total $t_C$ (hr) | $T_C$ (° C.) | Yield | Assay |
|---|---|---|---|---|---|---|---|---|---|
| 4 | 12.35 g | 1.42 g | Ethyl acetate 10.6 ml | n-Hexane 63.4 ml | 0.1 N NaOH 148 ml | 11 | +20--10 | 82.8% | 82.85% |
| 5 | 11.47 g | 1.42 g | Ethyl acetate 9.8 ml | n-Hexane 59 ml | 0.1 N $NH_3$ 137.6 ml | 62 | +25-0 | 79.19% | 82.55% |
| 6 | 11.72 g | 1.42 g | Ethyl acetate 6.4 ml | n-Hexane 63.9 ml | 0.1 N $NH_3$ 140.64 ml | 62 | +25-0 | 82.84% | 79.20% |
| 7 | 12.17 g | 1.42 g | Ethyl acetate 10.4 ml | n-Hexane 62.6 ml | 0.1 N $(C_2H_5)_3N$ 144.2 ml | 62 | +25-0 | 85.76% | 85.03% |
| 8 | 12.94 g | 1.42 g | Ethyl acetate 7 ml | Cyclohexane 70.6 ml | 0.1 N $(C_2H_5)_3N$ 155.3 ml | 62 | +25-0 | 82.98% | 82.18% |
| 9 | 13.28 g | 1.42 g | Ethyl acetate 11.4 ml | n-Hexane 68.3 ml | 0.1 N $(C_2H_5)_3N$ 159.4 ml | 50 | +25-0 | 72.84% | 75.64% |
| 10 | 14.72 g | 1.42 g | Ethyl acetate 12.6 ml | n-Hexane 75.8 ml | 0.1 N $(C_2H_5)_3N$ 176 ml | 32 | +25-0 | 74.74% | 84.81% |
| 11 | 11.36 g | 1.42 g | Ethyl acetate 9.7 ml | n-Hexane 58.4 ml | 0.1 N $(C_2H_5)_3N$ 136.3 ml | 50 | +25-0 | 71.64% | 80.89% |
| 12 | 11.39 g | 1.42 g | Ethyl acetate 9.8 ml | n-Hexane 58.6 ml | 0.1 N $(C_2H_5)_3N$ 136.7 ml | 50 | +25-0 | 88.32% | 83.68% |
| 13 | 20.93 g | 2.23 g | Ethyl acetate 17.9 ml | n-Hexane 107.8 ml | 0.1 N $(C_2H_5)_3N$ 251.2 ml | 62 | +25-0 | 91.2% | 86.49% |
| 14 | 20.17 g | 2.23 g | Ethyl acetate 17.3 ml | n-Hexane 103.7 ml | 0.1 N $(C_2H_5)_3N$ 242 ml | 62 | +25-0 | 62.7% | 83.34% |
| 15 | 19.15 g | 2.23 g | Ethyl acetate 16.4 ml | n-Hexane 98.5 ml | 0.1 N $(C_2H_5)_3N$ 229.8 ml | 62 | +25-0 | 91.2% | 88.05% |
| 16 | 20.4 g | 2.23 g | Ethyl acetate 8.7 ml | n-Hexane 52.5 ml | 0.1 N $(C_2H_5)_3N$ 122.4 ml | 62 | +25-0 | 91.2% | 88.06% |
| 17 | 18.78 g | 2.23 g | Ethyl acetate 4 ml | n-Hexane 24.2 ml | 0.1 N $(C_2H_5)_3N$ 56 ml | 62 | +25-0 | 86.64% | 86.90% |
| 18 | 4.56 g | 0.557 g | Acetonitrile 3.9 ml | n-Hexane 23.45 ml | 0.1 N $(C_2H_5)_3N$ 54.7 ml | 18 | +25-+20 | 79.92% | 83.46% |
| 19 | 4.62 g | 0.557 g | n-Butanol 3.96 ml | n-Hexane 23.76 ml | 0.1 N $(C_2H_5)_3N$ 55.44 ml | 18 | +25-+15 | 63.12% | 88.72% |
| 20 | 4.58 g | 0.557 g | Acetone 3.93 ml | n-Hexane 23.55 ml | 0.1 N $(C_2H_5)_3N$ 54.96 ml | 18 | +30-+20 | 87.07% | 82.56% |
| 21 | 4.62 g | 0.557 g | Isobutanol 3.75 ml | n-Hexane 22.5 ml | 0.1 N $(C_2H_5)_3N$ 52.44 ml | 18 | +25-+10 | 67.34% | 89.78% |
| 22 | 4.84 g | 0.557 g | Isopropanol 4.15 ml | n-Hexane 24.9 ml | 0.1 N $(C_2H_5)_3N$ 58.08 ml | 18 | +25-+20 | 80.26% | 83% |
| 23 | 4.54 g | 0.557 g | Ethanol 3.89 ml | n-Hexane 23.35 ml | 0.1 N $(C_2H_5)_3N$ 54.48 ml | 18 | +35-+20 | 76.92% | 82.13% |
| 24 | 4.43 g | 0.525 g | n-Propanol 3.79 ml | n-Hexane 22.78 ml | 0.1 N $(C_2H_5)_3N$ 53.16 ml | 18 | +25-+15 | 75.6% | 84.79% |
| 25 | 4.34 g | 0.525 g | Methanol 3.72 ml | n-Hexane 22.32 ml | 0.1 N $(C_2H_5)_3N$ 52.08 ml | 18 | +25-+20 | 77.16% | 78.18% |
| 26 | 3.84 g | 0.525 g | Diisopropyl ether 3.29 ml | n-Hexane 19.74 ml | 0.1 N $(C_2H_5)_3N$ 52.08 ml | 18 | +25-+10 | 59.52% | 72.35% |

EXAMPLE 3

Fermentation broth containing ascomycin was processed according to example 1. The process resulted in 60% yield for crude ascomycin.

The invention claimed is:

1. A method of crystallizing a macrolide from a macrolide starting material comprising the steps of:
   a) combining, in a crystallization vessel, a macrolide starting material, a polar solvent, a hydrocarbon solvent, and water, whereby at least two phases are formed, at least one of which is a water-rich phase, and wherein the pH of the water-rich phase is at least about 7,
   b) maintaining the combination at for at least 1 hour, whereby a macrolide-rich phase is formed from which the macrolide crystallizes.

2. The method of claim 1 further comprising the step of isolating the macrolide that crystallizes.

3. The method of claim 1 wherein the combination of step b is maintained at a temperature of from about −15° C. to about 50° C.

4. The method of claim 3 wherein the combination of step b is maintained at a temperature of from about −5° C. to about 40° C.

5. The method of claim 4 wherein the combination of step b is maintained at a temperature of from about −2° C. and about 35° C.

6. The method of claim 1 wherein the combination of step b is maintained for between 48 and 100 hours.

7. The method of claim 1 wherein the polar solvent is selected from the group consisting of alcohols, esters, nitriles and ethers.

8. The method of claim 7 wherein the poiar solvent is selected from the group consisting of ethyl acetate, acetonitrile, methanol, ethanol, n-propanol, iso-propanol, n-butanol, iso-butanol, acetone, diisopropyl ether, dimethyl formamide, and dimethyl acetamide.

9. The method of claim 8 wherein the polar solvent is ethyl acetate.

10. The method of claim 1 wherein the hydrocarbon solvent is selected from the group consisting of n-hexane, n-heptane, octane, iso-octane cyclohexane, methylcyclohexane, benzene, toluene, and xylene.

11. The method of claim 10 wherein the hydrocarbon solvent is n-hexane.

12. The method of claim 1 wherein the pH of the water-rich phase is about 8 or higher.

13. The method of claim 1 wherein the water comprises a base selected from NaOH, KOH, Ca(OH)$_2$, NH$_3$, Et$_3$N, diethylamine and pyridine.

14. The method of claim 1 wherein the macrolide is selected from the group consisting of tacrolimus, sirolimus, pimecrolimus, everolimus, and ascomycin.

15. A method of crystallizing a macro lide from a macrolide starting material comprising the steps of:
    a) combining a concentrate residue from whole-broth extraction of macrolide-containing biomatter in a polar solvent with a hydrocarbon solvent, and water, whereby at least two phases are formed, at least one of which is a water-rich phase, and wherein the pH of the water-rich phase is at least about 7,
    b) maintaining the combination at for at least 1 hour, whereby a macrolide-rich phase is formed from which the macrolide crystallizes.

16. The method of claim 15 further comprising the step of isolating the macrolide that crystallizes.

17. The method of claim 15 wherein the combination of step b is maintained at a temperature of from about −15° C. to about 50° C.

18. The method of claim 17 wherein the combination of step b is maintained at a temperature of from about −5° C. to about 40° C.

19. The method of claim 18 wherein the combination of step b is maintained at a temperature of from about −2° C. and about 35° C.

20. The method of claim 15 wherein the combination of step b is maintained for between 48 and 100 hours.

21. The method of claim 15 wherein the poiar solvent is selected from the group consisting of alcohols, esters, nitriles and ethers.

22. The method of claim 21 wherein the polar solvent is selected from the group consisting of ethyl acetate, acetonitrile, methanol, ethanol, n-propanol, iso-propanol, n-butanol, iso-butanol, acetone, diisopropyl ether, dimethyl formamide, and dimethyl acetamide.

23. The method of claim 22 wherein the polar solvent is ethyl acetate.

24. The method of claim 15 wherein the hydrocarbon solvent is selected from the group consisting of n-hexane, n-heptane, octane, iso-octane cyclohexane, methylcyclohexane, benzene, toluene, and xylene.

25. The method of claim 24 wherein the hydrocarbon solvent is n-hexane.

26. The method of claim 15 wherein the pH of the water-rich phase is about 8 or higher.

27. The method of claim 15 wherein the water comprises a base selected from NaOH, KOH, Ca(OH)$_2$, NH$_3$, Et$_3$N, diethylamine and pyridine.

28. The method of claim 15 wherein the macrolide is selected from the group consisting of tacrolimus, sirolimus, pimecrolimus, everolimus, and ascomycin.

29. A method of crystallizing a macrolide from a macrolide starting material comprising the steps of:
    a) combining, at a temperature of about 20° to about 25° C., macrolide starting material, ethyl acetate, n-hexane, and a water solution of a base selected from NaOH, KOH, Ca(OH)$_2$, NH$_3$, (C$_2$H$_5$)$_3$N, diethylamine and pyridine whereby at least two phases are formed, one of which is a water-rich phase, wherein the pH of the water-rich phase is >about 7,
    b) maintaining the combination at a temperature of about 20° C. to about 25° C. for at least 1 hour, whereby a macrolide-rich phase is formed from which macrolide crystallizes,
    c) maintaining the combination at a temperature of about 0° C. to about 20° C. for at least 1 hour, and
    d) recovering the macrolide that crystallizes.

30. The method of claim 29 wherein the macrolide is selected from the group consisting of tacrolimus, sirolimus, pimecrolimus, everolimus, and ascomycin.

31. The method of claim 29 wherein the pH of the water-rich phase is about 8 or higher.

32. A method of crystallizing a macrolide from a macrolide starting material comprising the steps of:
    a) combining, at a temperature of about 20° to about 25° C., a concentrate residue from whole-broth extraction of macrolide-containing biomatter in ethyl acetate, n-hexane, and a water solution of a base selected from NaOH, KOH, Ca(OH)$_2$, NH$_3$, (C$_2$H$_5$)$_3$N, diethylamine and pyridine whereby at least two phases are formed, one of which is a water-rich phase, wherein the pH of the water-rich phase is >about 7,
    b) maintaining the combination at a temperature of about 20° C. to about 25° C. for at least 1 hour, whereby a macrolide-rich phase is formed from which macrolide crystallizes,
    c) maintaining the combination at a temperature of about 0° C. to about 20° C. for at least 1 hour, and
    d) recovering the macrolide that crystallizes.

33. The method of claim 32 wherein the macrolide is selected from the group consisting of tacrolimus, sirolimus, pimecrolimus, everolimus, and ascomycin.

34. The method of claim 32 wherein the pH of the water-rich phase is about 8 or higher.

35. In a method for crystallizing a macrolide from a macrolide starting material, the step of combining the macrolide starting material, a polar solvent, a hydrocarbon solvent, and water, whereby at least two phases are formed, at least one of which is water rich, wherein the pH of the water-rich phase is at least about 7.

36. In a method for crystallizing a macrolide from a concentrate residue from whole-broth extraction of macrolide-containing biomatter in a polar solvent, the step of combining the macrolide concentrate in the polar solvent, a hydrocarbon solvent, and water, whereby at least two phases are formed, at least one of which is water rich, wherein the pH of the water-rich phase is at least about 7.

* * * * *